US008016589B2

(12) United States Patent
Veenstra et al.

(10) Patent No.: US 8,016,589 B2
(45) Date of Patent: Sep. 13, 2011

(54) METHOD OF STARTING UP A DIRECT HEATING SYSTEM FOR THE FLAMELESS COMBUSTION OF FUEL AND DIRECT HEATING OF A PROCESS FLUID

(75) Inventors: Peter Veenstra, Sugar Land, TX (US); Abdul Wahid Munshi, Houston, TX (US)

(73) Assignee: Shell Oil Company, Houston, TX (US)

( * ) Notice: Subject to any disclaimer, the term of this patent is extended or adjusted under 35 U.S.C. 154(b) by 830 days.

(21) Appl. No.: 11/371,890

(22) Filed: Mar. 9, 2006

(65) Prior Publication Data

US 2006/0222578 A1  Oct. 5, 2006

Related U.S. Application Data (60) Provisional application No. 60/660,448, filed on Mar. 10, 2005.

(51) Int. Cl.
*F23N 5/20* (2006.01)
*B01J 19/00* (2006.01)
*E21B 36/02* (2006.01)
*E21B 43/24* (2006.01)
*F22B 7/00* (2006.01)

(52) U.S. Cl. ............... 431/6; 422/198; 166/59; 122/156

(58) Field of Classification Search .......... 166/57, 166/59, 65.1, 66, 250, 251.1, 256, 257, 302; 431/6, 11, 181, 207, 243; 126/91 A; 422/46, 422/182, 197, 198, 200, 204, 215
See application file for complete search history.

(56) References Cited

U.S. PATENT DOCUMENTS

| 1,920,124 A | 7/1933 | Gillis |
| 2,772,737 A | 12/1956 | Bond et al. .................. 166/22 |
| 2,819,761 A | 1/1958 | Popham et al. ............... 166/39 |
| 2,902,270 A | 9/1959 | Salomonsson et al. ......... 262/3 |
| 3,113,623 A | 12/1963 | Krueger ........................ 166/59 |
| 3,376,932 A | 4/1968 | Hunt ............................ 166/59 |

(Continued)

FOREIGN PATENT DOCUMENTS

CN    87103900    12/1988

(Continued)

OTHER PUBLICATIONS

Khimicheskaya Entsiklopediya, M., Great Russian Encyclopedia. 508, with English translation.

*Primary Examiner* — Steven B McAllister
*Assistant Examiner* — Frances H Kamps (57) ABSTRACT

Included is a method of starting up a direct heating device having a fuel introduction zone, a combustion zone and a process zone that is in heat exchange relationship with said combustion zone. Prior to the introduction of a fuel fluid into said combustion zone, an oxidant fluid, having a high temperature, is passed through the combustion zone for a warm-up time period sufficient to raise the temperature of the direct heating device to a desired temperature. Steam or a process fluid is passed through the process zone followed by the introduction of a fuel fluid into the fuel introduction zone. After the device has been heated up a process fluid is introduced through the process zone. Thereafter, the introduction of steam through the process zone may be stopped.

18 Claims, 4 Drawing Sheets

U.S. PATENT DOCUMENTS

| | | | | |
|---|---|---|---|---|
| 3,519,396 | A | 7/1970 | Eagle et al. | 23/277 |
| 3,527,052 | A | 9/1970 | Bryce | 60/39.65 |
| RE26,990 | E | 11/1970 | Bongiorno | 252/373 |
| 3,777,717 | A * | 12/1973 | Mach et al. | 122/156 |
| 3,810,732 | A * | 5/1974 | Koch | 431/7 |
| 4,029,146 | A | 6/1977 | Hart et al. | 165/166 |
| 4,104,018 | A | 8/1978 | McKay | 432/29 |
| 4,189,294 | A * | 2/1980 | Rice et al. | 431/7 |
| 4,273,188 | A * | 6/1981 | Vogel et al. | 166/256 |
| 4,321,131 | A * | 3/1982 | Lowe | 208/130 |
| 4,353,712 | A | 10/1982 | Marion et al. | 48/197 R |
| 4,378,206 | A * | 3/1983 | Kullendorff et al. | 431/170 |
| 4,400,179 | A | 8/1983 | Marion et al. | 48/86 R |
| 4,692,306 | A | 9/1987 | Minet et al. | 422/49 |
| 4,716,858 | A * | 1/1988 | Bartels | 122/448.1 |
| 4,748,940 | A * | 6/1988 | Honig | 122/4 D |
| 4,818,371 | A * | 4/1989 | Bain et al. | 208/106 |
| 4,909,808 | A | 3/1990 | Voecks | 48/94 |
| 4,928,605 | A | 5/1990 | Suwa et al. | 110/261 |
| 5,008,085 | A * | 4/1991 | Bain et al. | 422/109 |
| 5,154,599 | A | 10/1992 | Wunning | 431/215 |
| 5,181,990 | A | 1/1993 | Arisaki et al. | 196/110 |
| 5,255,742 | A * | 10/1993 | Mikus | 166/303 |
| 5,306,481 | A | 4/1994 | Mansour et al. | 423/652 |
| 5,321,191 | A | 6/1994 | Alagy et al. | 585/648 |
| 5,330,970 | A | 7/1994 | Reid et al. | 507/90 |
| 5,404,952 | A * | 4/1995 | Vinegar et al. | 166/303 |
| 5,424,095 | A | 6/1995 | Clark et al. | 427/237 |
| 5,427,655 | A | 6/1995 | Woebcke et al. | 196/138 |
| 5,433,271 | A * | 7/1995 | Vinegar et al. | 166/272.1 |
| 5,446,229 | A | 8/1995 | Taylor et al. | 585/648 |
| 5,463,159 | A | 10/1995 | Callejas et al. | 585/648 |
| 5,513,981 | A | 5/1996 | Harbeck et al. | 431/263 |
| 5,523,502 | A | 6/1996 | Rubin | 585/324 |
| 5,536,488 | A | 7/1996 | Mansour et al. | 423/652 |
| 5,554,347 | A | 9/1996 | Busson et al. | 422/204 |
| 5,559,510 | A | 9/1996 | Strong, III et al. | 340/954 |
| 5,567,305 | A | 10/1996 | Jo | 208/48 R |
| 5,600,051 | A | 2/1997 | Baker et al. | 585/648 |
| 5,743,723 | A | 4/1998 | Iatrides et al. | 431/8 |
| 5,862,858 | A * | 1/1999 | Wellington et al. | 166/59 |
| 5,871,343 | A | 2/1999 | Baukal, Jr. et al. | 431/10 |
| 5,899,269 | A * | 5/1999 | Wellington et al. | 166/58 |
| 5,997,594 | A | 12/1999 | Edlund et al. | 48/76 |
| 6,153,152 | A | 11/2000 | Ruhl et al. | 422/197 |
| 6,221,117 | B1 | 4/2001 | Edlund et al. | 48/76 |
| 6,269,882 | B1 * | 8/2001 | Wellington et al. | 166/303 |
| 6,296,686 | B1 | 10/2001 | Prasad et al. | 95/51 |
| 6,402,988 | B1 | 6/2002 | Gottzmann et al. | 252/373 |
| 6,749,021 | B2 * | 6/2004 | Vinegar et al. | 166/245 |
| 6,783,741 | B2 | 8/2004 | Edlund et al. | 422/191 |
| 6,796,789 | B1 * | 9/2004 | Gibson et al. | 431/2 |
| 6,835,360 | B2 * | 12/2004 | Warren | 422/629 |
| 6,877,554 | B2 * | 4/2005 | Stegemeier et al. | 166/245 |
| 6,951,247 | B2 | 10/2005 | De Rouffignac et al. | 166/245 |
| 6,966,372 | B2 | 11/2005 | Wellington et al. | 166/245 |
| 7,025,940 | B2 * | 4/2006 | Shah et al. | 422/198 |
| 7,037,472 | B2 | 5/2006 | Komiya et al. | 422/197 |
| 7,063,145 | B2 * | 6/2006 | Veenstra et al. | 166/250.01 |
| 7,108,730 | B2 * | 9/2006 | Shah et al. | 48/203 |
| 7,121,342 | B2 * | 10/2006 | Vinegar et al. | 166/302 |
| 7,364,812 | B2 * | 4/2008 | Taylor et al. | 429/423 |
| 7,503,761 | B2 * | 3/2009 | Butler | 431/7 |
| 7,841,407 | B2 * | 11/2010 | Wellington et al. | 166/267 |
| 2002/0015670 | A1 | 2/2002 | Shah et al. | 422/198 |
| 2002/0027001 | A1 | 3/2002 | Wellington et al. | 166/59 |
| 2003/0101650 | A1 | 6/2003 | Okada et al. | 48/62 R |
| 2003/0101651 | A1 | 6/2003 | Weedon | 48/197 R |
| 2003/0182858 | A1 * | 10/2003 | Shah et al. | 48/127.9 |
| 2004/0022724 | A1 | 2/2004 | Robb | 423/651 |
| 2004/0033455 | A1 | 2/2004 | Tonkovich et al. | 431/7 |
| 2004/0057898 | A1 | 3/2004 | Singh et al. | 423/652 |
| 2004/0185398 | A1 | 9/2004 | Butler | 431/2 |
| 2004/0265224 | A1 | 12/2004 | Papavassiliou et al. | 423/651 |
| 2005/0178064 | A1 | 8/2005 | Maruko | 48/198.7 |
| 2005/0223643 | A1 * | 10/2005 | Butler | 48/94 |
| 2006/0000395 | A1 | 1/2006 | Joshi et al. | 110/267 |
| 2006/0021280 | A1 | 2/2006 | Hamilton et al. | 48/127.9 |
| 2006/0199119 | A1 | 9/2006 | Abbasi et al. | 431/8 |
| 2006/0199127 | A1 * | 9/2006 | Butler | 431/215 |
| 2006/0210468 | A1 | 9/2006 | Veenstra | 423/456 |
| 2006/0210936 | A1 * | 9/2006 | Veenstra | 431/11 |
| 2006/0222578 | A1 * | 10/2006 | Veenstra et al. | 422/198 |
| 2006/0248800 | A1 * | 11/2006 | Miglin et al. | 48/198.7 |
| 2007/0131411 | A1 | 6/2007 | Vinegar et al. | 166/59 |
| 2007/0151152 | A1 | 7/2007 | Mukai et al. | 48/127.9 |
| 2007/0175094 | A1 | 8/2007 | Reinke et al. | 48/127.9 |
| 2007/0196267 | A1 * | 8/2007 | Carpenter et al. | 423/648.1 |
| 2007/0254251 | A1 | 11/2007 | Cao et al. | 431/10 |
| 2008/0244973 | A1 | 10/2008 | Higashino | 48/127.9 |

FOREIGN PATENT DOCUMENTS

| | | |
|---|---|---|
| DE | 3222347 | 1/1983 |
| EP | 450872 | 10/1991 |
| EP | 0962422 | 12/1999 |
| GB | 2111181 | 5/1982 |
| JP | 271834 | 3/1990 |
| WO | WO2004022480 | 3/2004 |
| WO | WO2004059208 | 7/2004 |
| WO | WO2005090230 | 9/2005 |

* cited by examiner

METHOD OF STARTING UP A DIRECT HEATING SYSTEM FOR THE FLAMELESS COMBUSTION OF FUEL AND DIRECT HEATING OF A PROCESS FLUID

This invention claims the benefit of U.S. Provisional Application No. 60/660,448, filed Mar. 10, 2005 which is hereby incorporated by reference.

The invention relates to a method or methods of starting up a direct heating device or system.

A number of different types and designs of flameless combustion heating devices have been disclosed in the published literature. For instance, U.S. Pat. No. 5,255,742 discloses a method of heating a subterranean formation using a flameless combustion apparatus. The apparatus includes a fuel gas conduit containing a plurality of orifices. The fuel gas conduit is centralized within a combustion air conduit to form a first annulus between the fuel gas conduit and the combustion air conduit. The orifices provide for fluid communication between the fuel gas conduit and the first annulus. The combustion air conduit is centralized within a wellbore casing to thereby form a second annulus between the combustion air conduit and the wellbore casing. Fuel gas is introduced into the first annulus via the orifices of the fuel gas conduit to mix with the air and to combust within the first annulus. The first annulus formed by the combustion air conduit is in fluid communication with the second annulus between the combustion air conduit and the wellbore casing. This fluid communication provides a flow path for the combustion gases to be introduced into the second annulus and to travel up the second annulus to the surface to thereby provide heat that is transferred to a subterranean formation.

U.S. Publication No. 2003/0182858 describes a method for providing controlled heat to a process fluid by utilizing a flameless distributed combustion device. The device includes a fuel conduit containing a plurality of fuel nozzles distributed along its length and a surrounding oxidation chamber. A conduit that surrounds the fuel conduit forms the oxidation chamber. The device further includes a process chamber that surrounds the oxidation chamber. The fuel nozzles provide communication from within the fuel conduit to the oxidation chamber wherein the oxidant and fuel are mixed and the fuel combusted. The heat released from the combustion is transferred to the process chamber.

The aforementioned publications do not teach four-tube type flameless combustion heating devices for heating a process fluid, and they further do not recognize possible difficulties associated with the start-up of either a three-tube type or a four-tube type flameless combustion device from a cold start, especially when the tubes of the heating device are manifolded together into a heat exchanger system by the use of multiple tubesheets. One consideration when beginning the use of a flameless combustion device from a cold start is the possibility of an unstable combustion of the introduced fuel resulting from the introduction of various input streams into the cold device. Another consideration is the difficulty in the unsteady state operation of the flameless combustion device that may occur during a cold startup. Also, the effects of metal expansion of the flameless combustion device during a cold startup are a consideration.

It is, thus, an object of the invention to provide a method or process for starting up the use of a direct heating device after a period of non-use or from a cold start of the direct heating device.

Accordingly, provided is a method of starting up a direct heating system comprising a fuel introduction zone, a combustion zone and a process zone that is in heat exchange relationship with said combustion zone. This method comprises: passing a hot oxidant fluid through said combustion zone for a warm-up time period sufficient to raise the temperature of said direct heating system to a desired temperature; passing steam through said process zone for a second time period sufficient to adjust the temperature of said direct heating system to a second desired temperature; and after said desired temperature and said second desired temperature are reached, passing a fuel fluid comprising a fuel through said fuel introduction zone.

Another embodiment of the invention is a method of starting up a direct heating system comprising a fuel introduction zone, a combustion zone and a process zone that is in heat exchange relationship with said combustion zone. This method includes: passing a hot oxidant fluid through said combustion zone for a warm-up time period sufficient to raise the temperature of said direct heating system to a desired temperature; after said desired temperature is reached, passing a process stream comprising a process fluid through said process zone for a second time period sufficient to raise the temperature of said direct heating system to a second desired temperature; and after said second desired temperature is reached, passing a fuel fluid comprising a fuel through said fuel introduction zone.

The invention provides a method or process for starting up the use of a flameless combustion device or a direct heating system from a cold start. The direct heating system that is the subject of the startup procedure described herein is any type of heating system that provides for the combustion of a fuel and the direct transfer of the released heat energy into a process fluid.

The direct heating system of the invention includes those heating devices often referred to as a flameless combustion device or flameless combustion system or flameless distributed combustion (FDC) device or similar references, and it includes those integrated heating systems intended to provide for the combustion of fuels under conditions in which increments of fuel are introduced into a preheated oxidant stream at temperatures exceeding the auto-ignition temperature of the resultant mixture. The fuel and oxidant streams are to be rapidly mixed so that the combustion reaction is not limited in any way by a low mixing rate, and the velocity of the oxidant stream is to be such as to prevent the formation of a flame. The heat released by this so-called flameless combustion is to be transferred to a process fluid or stream passing through a process zone that is configured to be in heat exchange relationship with the combustion zone of the flameless combustion device by, for example, a process sleeve that surrounds either the combustion tube or the oxidant introduction tube, or both, of the flameless combustion device.

Some of the possible flameless combustion systems contemplated herein include three-tube and four-tube type flameless heating systems. A three-tube flameless heating device is a system that comprises a fuel introduction zone, a combustion zone, and a process zone. The fuel introduction zone is defined by a fuel tube having a plurality of apertures or orifices along its length that provide for the introduction of fuel into the combustion zone. A combustion tube that is external to and surrounds the fuel tube defines the combustion zone through which a preheated oxidant fluid is passed and mixed with the fuel that is introduced into the combustion zone via the apertures of the fuel tube. A process tube that is external to and surrounds the combustion tube defines the process zone through which a process fluid is passed. The process zone is further configured so that it is in heat exchange relationship with the combustion zone.

In some embodiments, a three tube type flameless heating system may include a fuel tube, an oxidant tube, and a process tube. The fuel tube has a length and a tube wall that define a fuel introduction zone wherein along said length and within said fuel introduction zone is included a fuel preheating zone and a combustion zone, wherein said fuel preheating zone includes a fuel inlet for introducing said fuel into said fuel preheating zone and a fuel outlet for introducing a preheated fuel from said fuel preheating zone into said combustion zone, and wherein along said combustion zone and through said tube wall is a plurality of apertures. The oxidant tube is external to and surrounds said fuel tube so as to thereby define an oxidant introduction zone along said length of said fuel tube, wherein said oxidant introduction zone includes an oxidant preheating zone and a fuel combustion zone, wherein said oxidant preheating zone includes an oxidant inlet for introducing an oxidant into said oxidant preheating zone end and an oxidant outlet for introducing a preheated oxidant from said oxidant preheating zone into said fuel combustion zone, and wherein said plurality of apertures provide for fluid communication between said combustion zone and said fuel combustion zone. The process tube that is external to and surrounds said oxidant tube so as to thereby define a process fluid introduction zone along said oxidant tube, wherein said process fluid introduction zone includes a process fluid heating zone and an oxidant/fuel heating zone, wherein said process fluid heating zone is in heat exchange relationship with said fuel combustion zone and includes a process fluid inlet for introducing said process fluid into said process fluid heating zone and a process fluid outlet for introducing a heated process fluid from said process fluid heating zone into said oxidant/fuel heating zone, and wherein said oxidant/fuel heating zone is in heat exchange relationship with both of said oxidant preheating zone and said fuel preheating zone and includes a discharge outlet for discharging from said oxidant/fuel heating zone said heated process fluid.

A three-tube type flameless heating system is described in detail in the concurrently filed patent application entitled "A Heat Transfer System for the Combustion of a Fuel and Heating of a Process Fluid and a Process that Uses Same" published as US 2006/0210468, the disclosure of which is incorporated in its entirety by reference into this specification.

A four-tube type flameless heating device is a system that comprises a fuel introduction zone, a combustion zone, an oxidant introduction zone, and a process zone. The fuel introduction zone is defined by a fuel tube having a plurality of apertures or orifices along its length that provide for the introduction of fuel into the combustion zone. A reaction or combustion tube that is external to and surrounds the fuel tube defines the combustion zone through which a preheated oxidant fluid is passed and mixed with the fuel that is introduced into the combustion zone via the apertures of the fuel tube. An oxidant introduction tube that is external to and surrounds the combustion tube and through which the oxidant fluid passes and is preheated prior to its introduction into the combustion zone defines the oxidant introduction zone. A process tube that is external to and surrounds the combustion tube defines the process zone through which a process fluid is passed. Both the process zone and the oxidant introduction zone are configured so that they are in heat exchange relationship, either directly or indirectly, with the combustion zone.

In some embodiments, a four-tube type flameless heating system may include in concentric relationship, a fuel introduction zone, a combustion zone, an oxidant introduction zone, and a process fluid zone, wherein said fuel introduction zone is defined by fuel introduction means for introducing fuel into said combustion zone that is defined by a reaction tube external to and surrounding said fuel introduction means, and wherein said oxidant introduction zone is defined by an oxidant tube external to and surrounding said reaction tube, and wherein said process fluid zone is defined by a process tube external to and surrounding said oxidant tube.

In some embodiments, a four-tube type flameless heating system may include a process system comprising a fuel tube having a fuel tube length and a fuel tube wall that define a fuel introduction zone, wherein said fuel tube includes a distal end and a fuel inlet end for introducing a fuel into said fuel introduction zone, and wherein along said fuel tube length and through said tube wall is a plurality of spaced apart apertures; a reaction tube having a reaction tube length and that is positioned external to and surrounding said fuel tube so as to thereby define a combustion zone along said fuel tube length, wherein said reaction tube has a reaction tube inlet end for receiving a preheated oxidant into said combustion zone and an exhaust end for discharging a combustion exhaust from said combustion zone, and wherein said plurality of spaced apart apertures provide for fluid communication between said fuel introduction zone and said combustion zone; an oxidant introduction tube having an oxidant introduction tube length and that is positioned external to and surrounding said reaction tube so as to thereby define an oxidant introduction zone along said reaction tube length, wherein said oxidant introduction tube has an oxidant introduction tube inlet end for introducing an oxidant into said oxidant introduction zone and an oxidant introduction tube outlet end for discharging said preheated oxidant from said oxidant introduction zone into said combustion zone through said oxidant introduction tube outlet end which is in fluid communication with said reaction tube inlet end, and wherein said oxidant introduction zone is in heat exchange relationship with said combustion zone; and a process tube that is positioned external to and surrounding said oxidant introduction tube so as to thereby define a process fluid zone along said oxidant introduction tube, wherein said process tube has a process fluid inlet end for introducing a process fluid into said process fluid zone and a process fluid outlet end for discharging a heated process fluid from said process fluid zone, and wherein said process fluid zone is in heat exchange relationship with said combustion zone.

A four-tube type flameless heating system is described in detail in the concurrently filed patent application entitled "A Multi-Tube Heat Transfer System for the Combustion of a Fuel and Heating of a Process Fluid and Use Thereof" published as US 2006/0210936, the disclosure of which is incorporated in its entirety by reference into this specification.

The inventive method is a procedure for starting up from a cold start a flameless heating system such as the three-tube and four-tube type flameless heating devices described above. The startup procedure requires a sequence of steps starting with the passing of a hot oxidant fluid into and through the combustion zone of the flameless heating device. The hot oxidant fluid is any suitable fluid that may be heated to a desired inlet temperature prior to its introduction into the combustion zone. In some embodiments of the invention, the oxidant may be heated by external means. For example, the oxidant may be heated by the process itself.

The hot oxidant fluid is passed through the combustion zone for a warm-up time period that is sufficient to raise the temperature of the flameless heating device to a desired temperature. The time it takes to raise the temperature of the flameless combustion device to the desired temperature will depend upon the mass of the device, the materials from which the device is manufactured, the starting temperature of the device, and the desired temperature of the device.

The desired temperature of the flameless combustion device may be determined or measured by any suitable means or method. A preferred approach for determining when the flameless combustion device has reached the desired temperature is by measuring the inlet temperature of the hot oxidant fluid that is introduced into the combustion zone of the flameless combustion device and measuring the outlet temperature of the hot oxidant fluid after it has passed through the combustion zone and when it exits the exhaust outlet.

Generally, when the hot oxidant fluid is first introduced into the combustion zone, the outlet temperature of the hot oxidant fluid as it exits the exhaust outlet of the flameless combustion device is significantly lower than the inlet temperature of the hot oxidant fluid as it is introduced through the combustion zone inlet of the flameless combustion device. This large temperature differential between the inlet temperature and outlet temperature of the hot oxidant fluid is due to the heat transfer from the hot oxidant fluid into the materials and mass of the flameless combustion device; but, as the hot oxidant fluid passes through the combustion zone, the flameless combustion device will heat up and the outlet temperature of the hot oxidant fluid will increase, thus, reducing the temperature differential between the inlet temperature and the outlet temperature of the hot oxidant fluid.

The temperature differential between the inlet temperature and outlet temperature may be monitored for a period of time to determine when the temperature of the flameless combustion device has reached a desired temperature. Either the aforementioned temperature differential or the absolute temperature of the hot oxidant fluid at the combustion zone exhaust outlet may be used as an indicator of the temperature of the flameless combustion device.

The hot oxidant fluid may be selected from any suitable fluid that can carry heat, i.e. having a sufficient heat capacity. The preferred oxidant fluid for use in the inventive method is an oxygen-containing fluid, such as air, with air being a preferred oxidant fluid. The hot oxidant fluid may also contain steam as a portion thereof. Thus, preferably, the hot oxidant fluid comprises air, and it further may comprise steam. It is recognized that the beginning of the warm-up step using the hot oxidant fluid does not preclude prior steps such as the passing of steam through any one or more of the zones of the flameless combustion device for purposes such as purging the system or even warm-up of the system. In some embodiments, process steps are carried out before the beginning of the warm-up step using the hot oxidant fluid. For example, steam may be passed through any one or more of the zones of the heat transfer system for purposes such as purging the system or even warm-up of the system.

The inlet temperature of the hot oxidant fluid may be at least as high as is necessary to provide for the desired heating of the flameless combustion device. In typical embodiments, the inlet temperature of the hot oxidant fluid may be in the range of from about 200° C. (392° F.) to about 2000° C. (3632° F.) or from about 260° C. (500° F.) to about 1000° C. (1832° F.), preferably, from about 360° C. (680° F.) to about 850° C. (1562° F.), and, most preferably, about 460° C. (860° F.) to about 725° C. (1337° F.).

When the hot oxidant fluid is first introduced into the combustion zone of the flameless combustion zone, the outlet temperature of the exhaust hot oxidant fluid will be, as noted above, significantly lower than its inlet temperature. The temperature differential will, however, narrow as the time during which the hot oxidant fluid is passed through the flameless combustion device increases. The desired temperature of the outlet temperature should exceed about 460° C. (860° F.), preferably, it is to exceed about 560° C. (1040° F.), and, most preferably, the desired temperature of the outlet of the combustion zone should exceed about 620° C. (1148° F.).

Once the desired temperature of the hot oxidant fluid exhaust is reached, in one embodiment of the startup procedure, steam as a process zone fluid is introduced and passed through the process zone of the flameless combustion device. The temperature of the process zone fluid is measured and monitored in the same or similar manner as is the temperature of the hot oxidant fluid of the combustion zone as described above.

The process zone inlet temperature of the steam process fluid may be that of superheated steam that exceeds about 425° C. (797° F.). It is preferred for the temperature of the steam that is introduced into the process zone to exceed about 510° C. (950° F.), and, most preferably, the inlet steam temperature exceeds about 560° C. (1040° F.). It is especially preferred for the steam to be superheated and have a temperature exceeding about 620° C. (1148° F.).

The steam is passed through the process zone for a second time period that is sufficient to adjust the temperature of the flameless combustion device to a second desired temperature. This second desired temperature may be determined by monitoring the temperature of the process zone fluid at the outlet of the process zone. The second desired temperature of the process zone outlet temperature should exceed about 460° C. (860° F.), preferably, it should exceed about 560° C. (1040° F.), and, most preferably, the second desired temperature at the outlet of the process zone should exceed about 620° C. (1148° F.).

Once either the desired temperature is reached or the second desired temperature is reached, or both the desired temperature and the second desired temperature are reached, a fuel fluid is introduced into the fuel introduction zone which passes through the fuel tube apertures into the combustion zone wherein it mixes with the hot oxidant fluid passing therethrough and combustion begins. The combustion mixture comprising the fuel fluid and the hot oxidant fluid is at a temperature above the auto-ignition temperature of the mixture. No additional hardware or electronics are needed to initiate or aid in the initiation of combustion. Sparks, igniters, glow plugs, and other similar items are not needed to initiate combustion.

Any suitable fluid that is combustible in the presence of an oxidant such as oxygen or air may be used as the fuel fluid. Examples of such fuels include hydrogen and hydrocarbons. Examples of hydrocarbons that may be used as fuel include those hydrocarbons having from one to six carbon atoms, including, methane, ethane, ethylene, propane, propylene, propyne, butane, butylenes, and butyne. Preferred fuels include those selected from the group consisting of hydrogen, methane, ethane and mixtures thereof.

The fuel that is initially introduced into the fuel introduction zone during the startup of the flameless combustion device may further comprise a proportion thereof that is steam. In this case, the fuel and steam mixture is passed through the fuel introduction zone and through its apertures into the combustion zone wherein the combustion of the fuel occurs. After a time period during which the combustion takes place, the steam is removed from the fuel and the flameless combustion device is permitted to continue to burn the fuel.

In another embodiment, steam is injected to purge the lines during heating. Fuel is introduced and the introduction of steam stops. Once the fuel ignites, a different fuel or mixture of fuels can be introduced, and this fuel or mixture of fuels may comprise steam. Another embodiment involves the startup without a steam purge that involves injecting a fuel without steam.

Once the desired temperature and second desired temperature are both reached, a process stream may then be introduced and passed through the process zone of the flameless combustion device. The process stream is introduced into the process zone either prior to the discontinuance of the introduction of the steam into the process zone, or after the discontinuance of the introduction of the steam into the process zone, or simultaneously with the discontinuance of the introduction of the steam into the process zone, and, thus, thereafter, the process fluid without added steam is then passed through the process zone. The startup of the flameless combustion device is complete once the fuel, the oxidant fluid and the process stream are being introduced into the respective zones. In some embodiments, the fuel may be a mixture of fuels and/or the fuel may comprise steam.

In another embodiment of the inventive startup procedure, instead of passing steam through the process zone after the desired temperature of the flameless combustion device is reached, a process stream is introduced and passed through the process zone of the flameless combustion device. Using a process stream instead of steam may be particularly useful in the situation where the process stream is one which is already or will be, under standard operation, at a reasonably high temperature or when the process stream is preheated before passing it through the process zone.

One example of an embodiment in which the process stream will be at a reasonably high temperature is when the flameless combustion device is to be used to introduce heat into a dehydrogenation process stream, such as an ethylbenzene dehydrogenation stream of a styrene manufacturing process. In this case, it is desirable for its temperature at the inlet of the process zone to have a temperature that exceeds about 425° C. (797° F.). It is preferred for the temperature of the process stream that is introduced into the process zone to exceed about 510° C. (950° F.), and, most preferably, the inlet process stream temperature exceeds about 560° C. (1040° F.). It is especially preferred for the process stream to have a temperature exceeding about 620° C. (1148° F.).

As with the use of the steam, the process stream is passed through the process zone for a time period that is sufficient to adjust the temperature of the flameless combustion device to a second desired temperature. This second desired temperature may be determined by monitoring the temperature of the process zone fluid at the outlet of the process zone. The second desired temperature of the process zone outlet temperature should exceed about 460° C. (860° F.), preferably, it should exceed about 560° C. (1040° F.), and, most preferably, the second desired temperature at the outlet of the process zone should exceed about 620° C. (1148° F.).

Once either the desired temperature or the second desired temperature, or both the desired temperature and second desired temperature, are reached a fuel is introduced into the fuel introduction zone and combustion within the combustion zone begins. The combustion mixture comprising the fuel fluid and the hot oxidant fluid is at a temperature above the auto-ignition temperature of the mixture. No additional hardware or electronics are needed to initiate or aid in the initiation of combustion. Sparks, igniters, glow plugs, and other similar items are not needed to initiate combustion.

The fuel that is initially introduced into the fuel introduction zone for this embodiment of the inventive startup procedure may further comprise a proportion thereof that is added steam. In this case, the fuel and added steam mixture is passed through the fuel introduction zone and through its apertures into the combustion zone wherein the combustion of the fuel occurs. After a time period during which the combustion takes place, the added steam is removed from the fuel and the flameless combustion device is permitted to continue to burn the fuel. The process stream of this embodiment of the inventive startup procedure may also additionally further comprise an amount of steam. Once the flameless combustion device is heated up, the proportion of the steam contained in the fuel fluid and the amount of steam contained in the process stream may be reduced.

Figure 1:
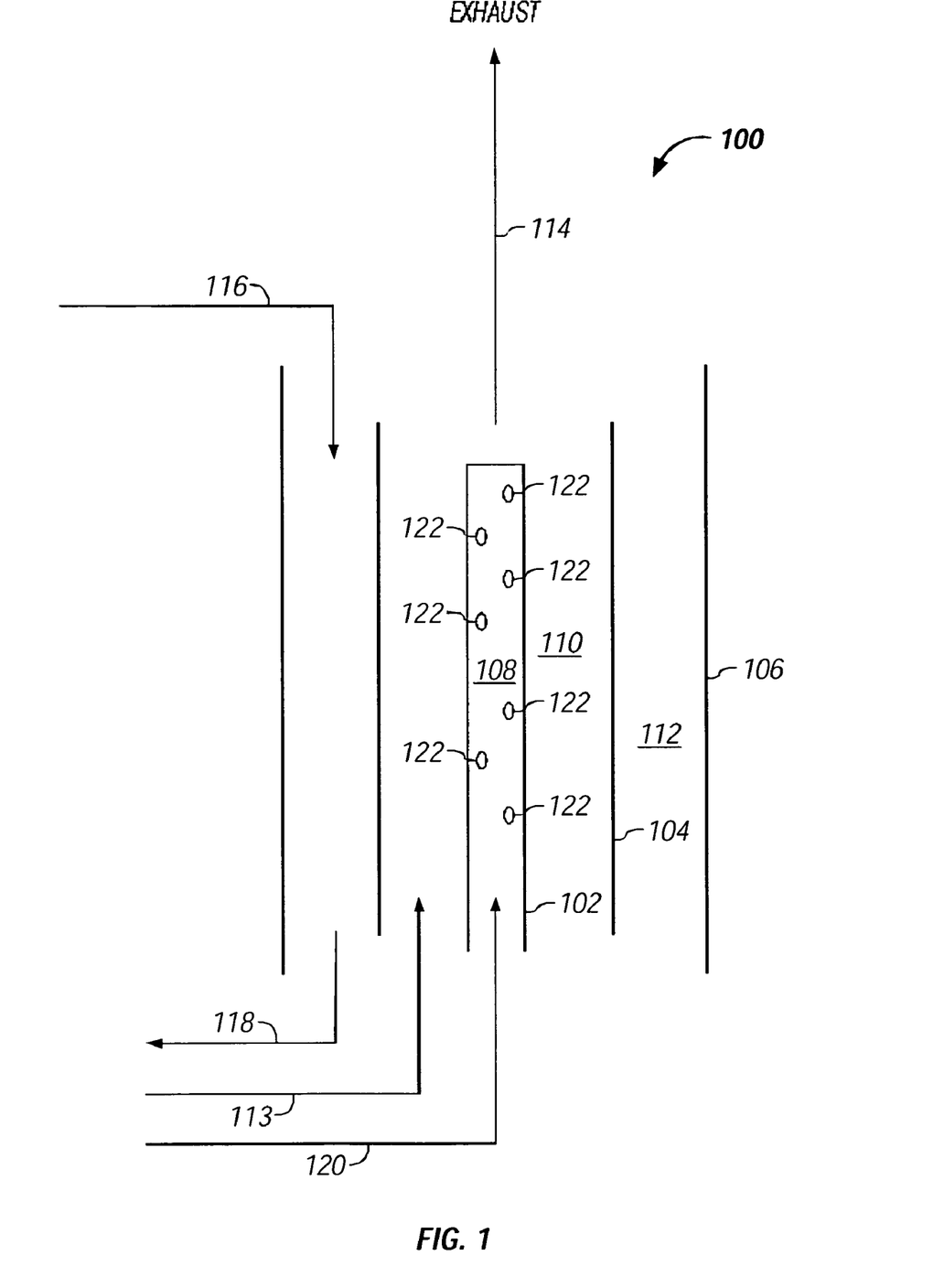
FIG. 1 is a simplified schematic representing a three-tube flameless combustion device that is the subject of the inventive start-up method.
Figure 1B:
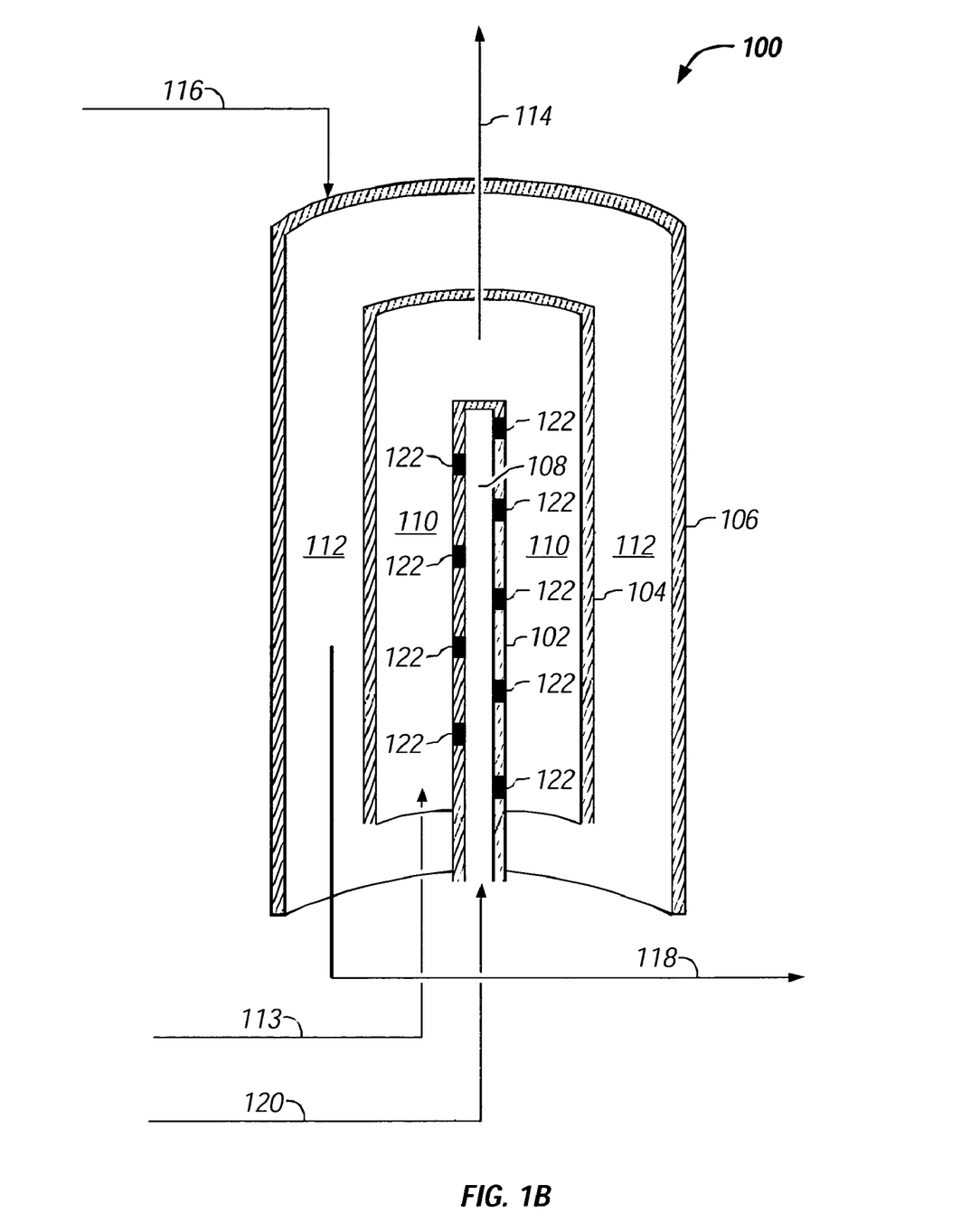
FIG. 1B is a simplified schematic representing an embodiment of a three-tube flameless combustion device that is the subject of the inventive start-up method.

Reference is now made to FIG. 1, which presents a simplified schematic of the tube arrangement of a three-tube type flameless combustion device 100.

One embodiment of the inventive startup procedure requires providing a three-tube flameless combustion device 100, having a fuel tube 102, a combustion tube 104, and a process tube 106 that respectively define a fuel introduction zone 108, a combustion zone 110, and a process zone 112.

In most instances, the startup of the three-tube flameless combustion device is from a cold start. A hot oxidant fluid, such as air, is introduced into the combustion zone 110 via combustion zone inlet conduit 113 and is passed through the combustion zone 110 for a warm-up time period sufficient to raise the temperature of the three-tube combustion device 100 to a desired temperature.

The desired temperature of the three-tube flameless combustion device 100 may be monitored and determined by the measurement of the outlet temperature of the hot oxidant fluid as it exits the combustion zone 110 via combustion zone outlet conduit 114. This combustion zone outlet temperature is related to and it may be used as an indicator of the temperature of the three-tube flameless combustion device 100 for the purpose of determining when the temperature of the three-tube flameless combustion device 100 is at the desired temperature.

Steam is introduced into the process zone 112 via process zone inlet conduit 116, and the steam passes through the process zone 112 for a second time period that is sufficient to adjust the temperature of the three-tube flameless combustion device 100 to a second desired temperature. The second desired temperature of the three-tube flameless combustion device may be monitored and determined by the measurement of the process side outlet temperature of the steam as it exits the process zone 112 via the process zone outlet conduit 118. This outlet temperature of the steam from the process zone 112 is related to and it may be used as an indicator of the temperature of the three-tube flameless combustion device 100 for the purpose of determining when the temperature of the three-tube flameless combustion device 100 is at the second desired temperature.

Once either the desired temperature is reached, or the second desired temperature is reached, or both the desired temperature and the second desired temperature are reached, a fuel fluid is introduced into the fuel introduction zone 108 via fuel introduction zone inlet conduit 120. The fuel fluid passes through the fuel introduction zone 108 and the apertures 122 and is introduced into combustion zone 110 wherein it is mixed with the hot oxidant fluid and combustion occurs. The exhaust from the combustion zone 110 passes from the combustion zone 110 via combustion zone outlet conduit 114.

Once the fuel is introduced into the combustion zone 110 and combustion occurs, the steam passing through process zone 112 may be replaced with a process fluid to be heated. Thus, a process stream, comprising a process fluid, is introduced into and passes through the process zone 112. The introduction of the process stream into the process zone 112 may be done simultaneously with the discontinuance of the introduction of the steam into the process zone 112, or prior to the discontinuance of the introduction of steam into the process zone 112, or after the discontinuance of the introduction of steam into the process zone 112, after which time, the startup of the three-tube flameless combustion device is substantially complete.

Figure 2:
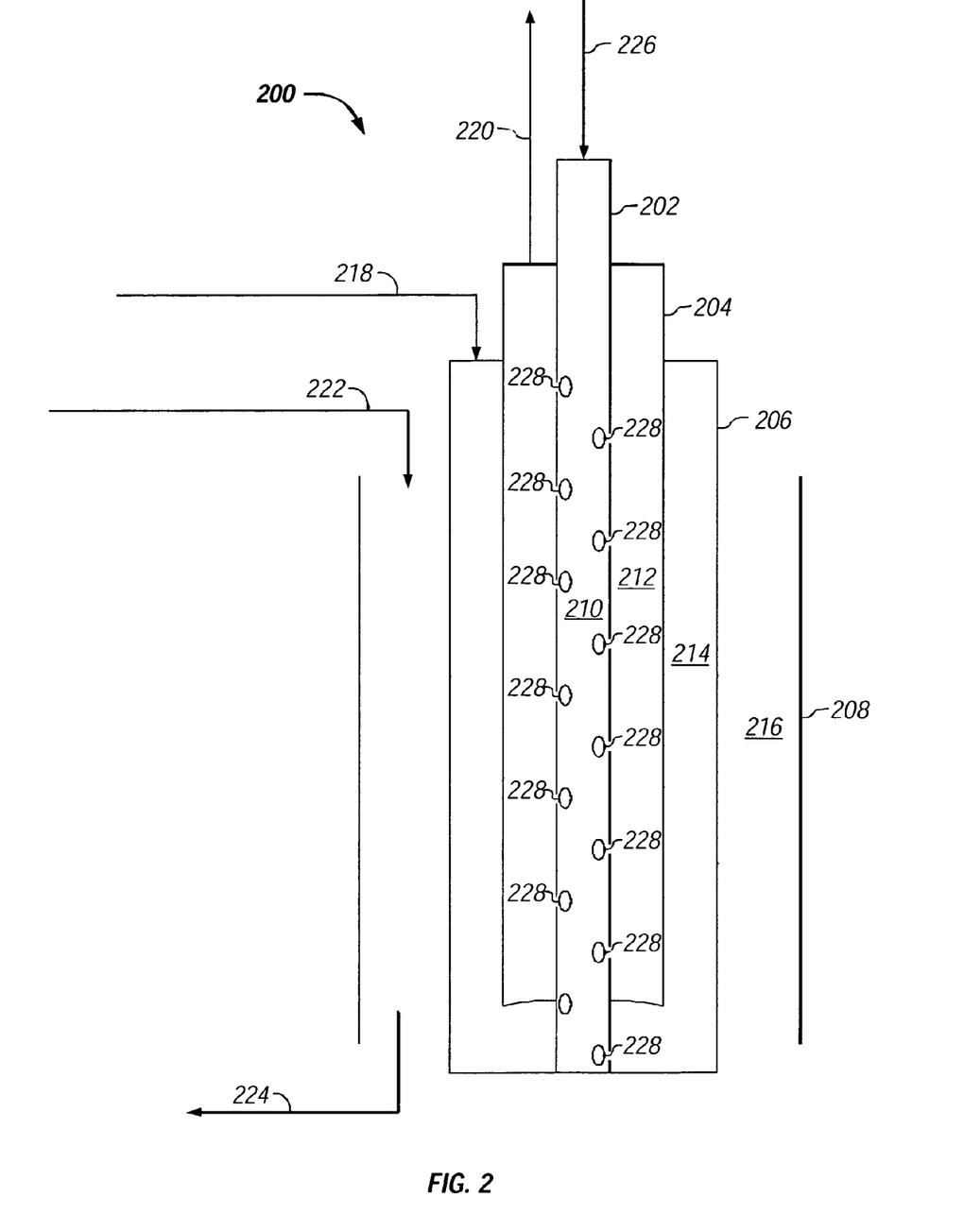
FIG. 2 is a simplified schematic of a four-tube flameless combustion device that is the subject of the inventive start-up method.
Figure 2B:
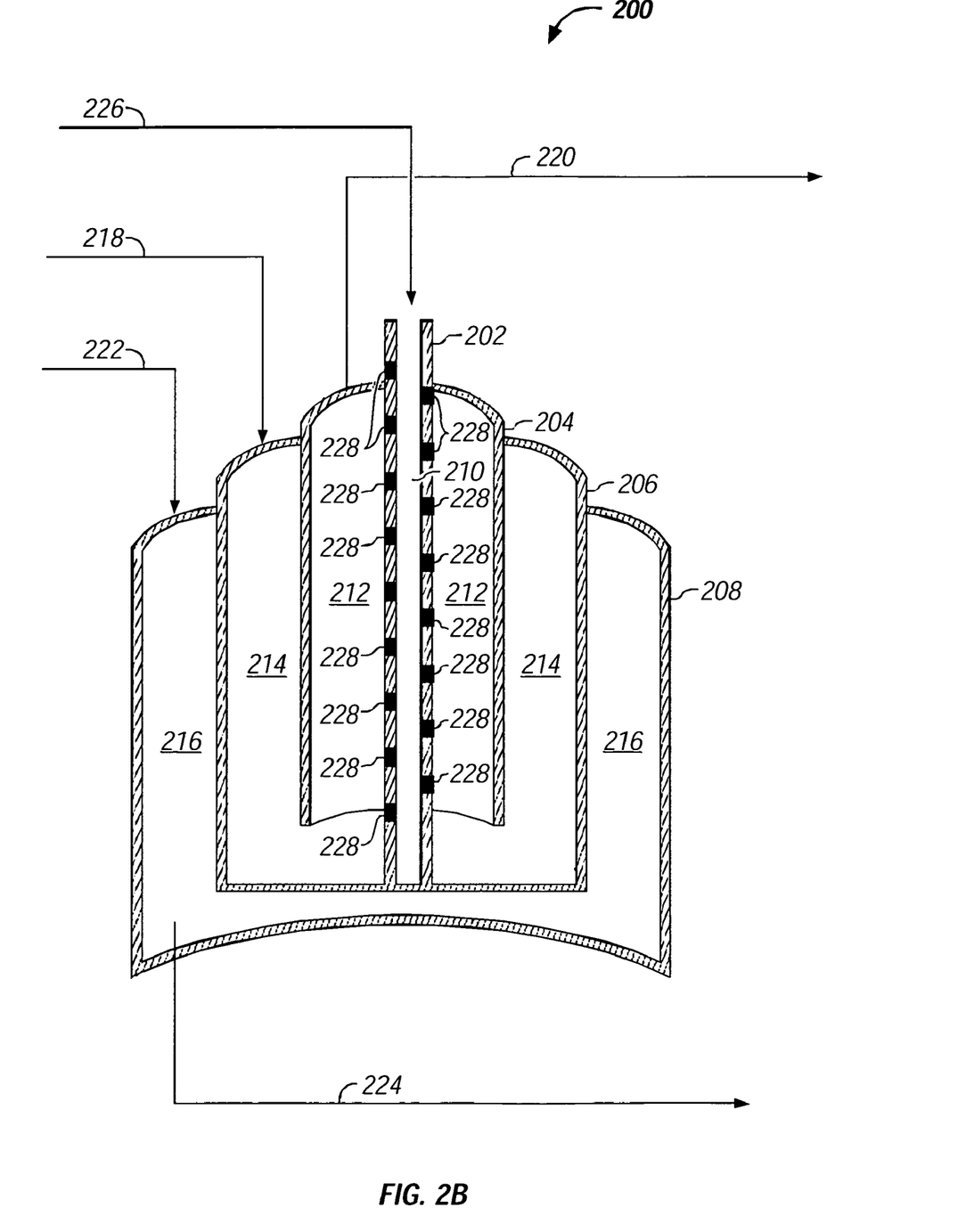
FIG. 2B is a simplified schematic representing an embodiment of a four-tube flameless combustion device that is the subject of the inventive start-up method.

Reference is now made to FIG. 2, which presents a simplified schematic of the tube arrangement of a four-tube type flameless combustion device 200. Another embodiment of the inventive startup procedure requires providing a four-tube flameless combustion device 200, having a fuel tube 202, a combustion tube 204, an oxidant introduction tube 206, and a process tube 208 that respectively define a fuel introduction zone 210, a combustion zone 212, an oxidant introduction zone 214, and a process zone 216.

In typical embodiments, the process zone is external to the oxidant introduction zone. Further, in typical embodiments, the oxidant introduction zone is external to the combustion zone. Further, in typical embodiments the combustion zone is external to the fuel introduction zone.

In most instances, the startup of the four-tube flameless combustion device is from a cold start in which a hot oxidant fluid, such as air, is introduced into the combustion zone 212 via the oxidant introduction zone inlet conduit 218 and oxidant introduction zone 214, and the hot oxidant fluid is then passed through the combustion zone 212 for a warm-up time period sufficient to raise the temperature of the four-tube combustion device 200 to a desired temperature.

The temperature of the four-tube flameless combustion device 200 may be monitored and determined by the measurement of the outlet temperature of the hot oxidant fluid as it exits the combustion zone 212 via combustion zone outlet conduit 220. This outlet temperature is related to and may be used as an indicator of the temperature of the four-tube flameless combustion device 200 for the purpose of determining when the temperature of the four-tube flameless combustion device 200 is at the desired temperature.

Steam is introduced into the process zone 216 via process zone inlet conduit 222, and the steam passes through the process zone 216 for a second time period that is sufficient to adjust the temperature of the four-tube flameless combustion device 200 to a second desired temperature. The second desired temperature of the four-tube flameless combustion device may be monitored and determined by the measurement of the process side outlet temperature of the steam as it exits the process zone 216 via the process zone outlet conduit 224. This outlet temperature of the steam from the process zone 216 is related to and may be used as an indicator of the temperature of the four-tube flameless combustion device 200 for the purpose of determining when the temperature of the four-tube flameless combustion device 200 is at the second desired temperature.

Once either the desired temperature is reached, or the second desired temperature is reached, or both the desired temperature and the second desired temperature are reached, a fuel fluid is introduced into the fuel introduction zone 210 via fuel introduction zone inlet conduit 226. The fuel fluid passes through the fuel introduction zone 210 and the apertures 228 and is introduced into combustion zone 212 wherein it is mixed with the hot oxidant fluid and combustion occurs. The exhaust from the combustion zone 212 passes from the combustion zone 212 via combustion zone outlet conduit 220.

Once the fuel is introduced into the combustion zone 212 and combustion occurs, the steam passing through process zone 216 may be replaced with a process fluid to be heated. Thus, a process stream, comprising a process fluid, is introduced into and passes through the process zone 216. The introduction of the process stream into the process zone 216 may be done simultaneously with the discontinuance of the introduction of the steam into the process zone 216, or prior to the discontinuance of the introduction of steam into the process zone 216, or after the discontinuance of the introduction of steam into the process zone 216, at which time, the startup of the four-tube flameless combustion device is substantially complete.

It is understood that while particular embodiments of the invention have been described herein, reasonable variations, modifications and adaptations thereof may be made that are within the scope of the described disclosure and the appended claims without departing from the scope of the invention as defined by the claims.

That which is claimed is:

1. A method of starting up a direct heating system comprising a fuel introduction zone, a combustion zone and a process zone that is in heat exchange relationship with said combustion zone, said method comprises:

passing a hot oxidant fluid through said combustion zone for a warm-up time period sufficient to raise the temperature of said direct heating system to a first desired temperature;

continuing to pass the hot oxidant fluid through the combustion zone:

passing steam through said process zone for a second time period sufficient to adjust the temperature of said direct heating system to a second desired temperature;

after said first desired temperature and said second desired temperature are reached, passing a fuel fluid comprising a fuel through said fuel introduction zone; and contacting the fuel fluid with the hot oxidant fluid;

wherein the step of continuing to pass the hot oxidant fluid through the combustion zone comprises continuously passing the hot oxidant fluid from the step of passing a hot oxidant fluid through said combustion zone for a warm-up time period until the step of passing a fuel fluid comprising a fuel through said fuel introduction zone.

2. A method as recited in claim 1, further comprising:

after said desired temperature and said second desired temperature are reached:

discontinuing the passing of said steam through said process zone; and passing a process stream comprising a process fluid through said process zone.

3. A method as recited in claim 2, wherein said fuel fluid further comprises a proportion of steam.

4. A method as recited in claim 3, further comprising:

reducing said proportion of steam in said fuel fluid.

5. A method as recited in 4, wherein said process stream further comprises an amount of steam.

6. A method as recited in claim 5, further comprising:

reducing said amount of steam in said process stream.

7. A method of starting up a direct heating system comprising a fuel introduction zone, a combustion zone and a process zone that is in heat exchange relationship with said combustion zone, said method comprises:

passing a hot oxidant fluid through said combustion zone for a warm-up time period sufficient to raise the temperature of said direct heating system to a first desired temperature;

continuing to pass the hot oxidant fluid through the combustion zone;

after said first desired temperature is reached, passing a process stream comprising a process fluid through said process zone for a second time period sufficient to raise the temperature of said direct heating system to a second desired temperature;

after said second desired temperature is reached, passing a fuel fluid comprising a fuel through said fuel introduction zone; and contacting the fuel fluid with the hot oxidant fluid;

wherein the step of continuing to pass the hot oxidant fluid through the combustion zone comprises continuously passing the hot oxidant fluid from the step of passing a hot oxidant fluid through said combustion zone for a warm-up time period until the step of passing a fuel fluid comprising a fuel through said fuel introduction zone.

8. A method as recited in claim 7, wherein said process stream further comprises an amount of steam.

9. A method as recited in claim 8, wherein said fuel fluid further comprises a proportion of steam.

10. A method as recited in claim 9, further comprising: reducing said proportion of steam in said fuel fluid.

11. A method as recited in claim 10, further comprising: reducing said amount of steam in said process stream.

12. A method of starting up a direct heating system comprising a fuel introduction zone, a combustion zone and a process zone that is in heat exchange relationship with said combustion zone, said method comprises:

passing a hot oxidant fluid through said combustion zone for a warm-up time period sufficient to raise the temperature of said direct heating system to a first desired temperature; and continuing to pass the hot oxidant fluid through the combustion zone;

after said first desired temperature is reached, passing steam through said process zone for a second time period sufficient to raise the temperature of said direct heating system to a second desired temperature;

after said first desired temperature and said second desired temperature are reached, passing a fuel fluid comprising a fuel through said fuel introduction zone; and contacting the fuel fluid with the hot oxidant fluid;

wherein the step of continuing to pass the hot oxidant fluid through the combustion zone comprises continuously passing the hot oxidant fluid from the step of passing a hot oxidant fluid through said combustion zone for a warm-up time period until the step of passing a fuel fluid comprising a fuel through said fuel introduction zone.

13. A method as recited in claim 12, further comprising: introducing a process stream comprising a process fluid through said process zone.

14. A method as recited in claim 13, wherein said process stream further comprises an amount of steam.

15. A method as recited in claim 14, wherein said fuel fluid further comprises a proportion of steam.

16. A method as recited in claim 15, further comprising: reducing said amount of steam in said process stream.

17. A method as recited in claim 16, further comprising: reducing said proportion of steam in said fuel fluid.

18. A method of starting up a direct heating device, said method comprises:

providing a direct heating device having a fuel introduction zone, a combustion zone and a process zone that is in heat exchange relationship with said combustion zone;

prior to the introduction of a fuel fluid into said combustion zone, passing an oxidant fluid, having a high temperature, through said combustion zone for a warm-up time period sufficient to raise the temperature of said direct heating device to a desired first temperature;

continuing to pass the hot oxidant fluid through the combustion zone;

passing superheated steam through said process zone;

prior to the introduction of said fuel fluid into said fuel introduction zone, passing steam through said fuel introduction zone;

introducing said fuel fluid at an incrementally increasing rate into said fuel introduction zone with said steam to a desired fuel fluid introduction rate and, thereafter, ceasing said passing of said steam through said fuel introduction zone;

contacting the fuel fluid with the hot oxidant fluid; and passing a process fluid with said superheated steam through said process zone and, thereafter, ceasing said passing of said superheated steam through said process zone;

wherein the step of continuing to pass the oxidant fluid having a high temperature through the combustion zone comprises continuously passing the oxidant fluid having a high temperature from the step of passing a oxidant fluid, having a high temperature, through said combustion zone for a warm-up time period until the step of introducing said fuel fluid at an incrementally increasing rate into said fuel introduction zone with said steam to a desired fuel fluid introduction rate.

* * * * *